(12) United States Patent
Fischer et al.

(10) Patent No.: US 6,316,659 B1
(45) Date of Patent: Nov. 13, 2001

(54) METHOD FOR PRODUCING CYCLOPENTANONE AND CYCLOPENTENE-1-CARBOXYLIC ACID AND THEIR ESTERS

(75) Inventors: Rolf Fischer, Heidelberg; Shelue Liang, Schifferstadt; Rolf Pinkos; Frank Stein, both of Bad Dürkheim, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/508,008

(22) PCT Filed: Aug. 27, 1998

(86) PCT No.: PCT/EP98/05442

§ 371 Date: Mar. 7, 2000

§ 102(e) Date: Mar. 7, 2000

(87) PCT Pub. No.: WO99/12883

PCT Pub. Date: Mar. 18, 1999

(30) Foreign Application Priority Data

Sep. 9, 1997 (DE) .............................. 197 39 441

(51) Int. Cl.$^7$ ............................ C07C 69/74; C07C 45/00
(52) U.S. Cl. ...................... 560/122; 562/504; 568/354
(58) Field of Search ................. 562/504; 560/122

(56) References Cited

U.S. PATENT DOCUMENTS

| 4,745,228 | 5/1988 | Decker . |
| 4,822,920 | 4/1989 | Lermer et al. . |

FOREIGN PATENT DOCUMENTS

| 251 111 | 1/1988 | (EP) . |
| 266 687 | 5/1988 | (EP) . |

OTHER PUBLICATIONS

Heterocycles, vol. 42, No. 1, 1996, 423–435.
Makromol.Chem. 190,929–938 (1989) 929–938.
Heteropoly Compounds of Molybdenum and Tungsten, Tsigdinos 1–64, 1977.
Chem.Abst. XP–002091058, vol. 7 (1973) 8/6 No. 5.

Primary Examiner—Paul J. Killos
(74) Attorney, Agent, or Firm—Keil & Weinkauf

(57) ABSTRACT

A process for preparing cyclopentanone and cyclopentene-1-carboxylic acid or an ester thereof of the formula I

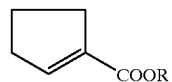

I where R is hydrogen or an aliphatic radical having 1–6 carbon atoms or a cycloaliphatic, araliphatic or aromatic radical having 6–12 carbon atoms comprises heating a compound of the formula II

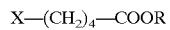

X—(CH$_2$)$_4$—COOR    II where X is formyl or hydroxymethyl and R is defined as above, and/or a compound which is converted into a compound of the formula II by reaction with water or alcohols ROH under the reaction conditions to from 200 to 450° C. in the gas or liquid phase in the presence of a heterogeneous oxidic catalyst.

12 Claims, No Drawings

METHOD FOR PRODUCING CYCLOPENTANONE AND CYCLOPENTENE-1-CARBOXYLIC ACID AND THEIR ESTERS

The present invention relates to a process for preparing cyclopentanone and cyclopentene-1-carboxylic acid and an ester thereof by reacting 5-formylvaleric acid and an ester thereof and/or 6-hydroxycaproic acid and an ester thereof and/or a compound which is converted into 6-hydroxycaproic acid or an ester thereof by reaction of water and alcohols under the reaction conditions, alone or as a mixture with adipic esters, over oxidic catalysts at from 200 to 450° C. in the gas or liquid phase.

EP-A-251 111 discloses the preparation of cyclopentanone by reacting adipic diesters over oxidic catalysts at an elevated temperature in the gas or liquid phase. Furthermore, EP-A-266 687 discloses the use of zeolitic catalysts or phosphate catalysts for this reaction.

It is an object of the present invention to prepare cyclopentanone from starting materials which are even more easily obtainable than adipic diesters (readily obtainable by esterification of adipic acid), even at the cost of the coproduction of a further product of value.

This product of value is cyclopentene-1-carboxylic acid or its esters, which have previously been prepared in a rather complicated way by reduction of cyclopentanone-2-carboxylic esters to give cyclopentanol-2-carboxylic esters and subsequent elimination of water (Heterocycles 47 (1996), 423–425.

We have found that this object is achieved according to the invention by a process for preparing cyclopentanone and cyclopentene-1-carboxylic acid or an ester thereof of the formula I

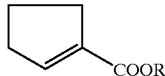
    COOR                                                              I where R is hydrogen or an aliphatic radical having 1–6 carbon atoms or a cycloaliphatic, araliphatic or aromatic radical having 6–12 carbon atoms, which comprises heating a compound of the formula II

X—(CH$_2$)$_4$—COOR                                                  II where X is formyl or hydroxymethyl and R is defined as above, and/or a compound which is converted into a compound of the formula II by reaction with water or alcohols ROH under the reaction conditions to from 200 to 450° C. in the gas or liquid phase in the presence of a heterogeneous oxidic catalyst.

In a particular embodiment of the process, a mixture of a compound of the formula II and an adipic diester of the formula III

ROCO—(CH$_2$)$_4$—COOR                                              III, where R is defined as above, is reacted, in particular a mixture as obtained by the process according to DE-A 19 607 954.

The reaction according to the invention can be represented, for example for the conversion of methyl 5-formylvalerate to cyclopentanone and methyl cyclopentene-1-carboxylate, by the following reaction equation.

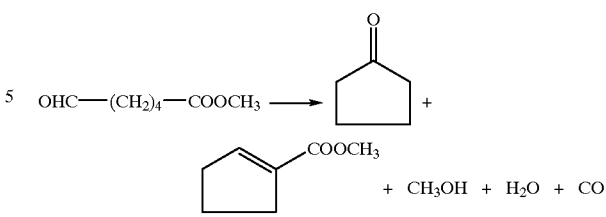

When 6-hydroxycaproic acid or an ester thereof or a compound which is converted into 6-hydroxycaproic acid or an ester thereof, e.g. ε-caprolactone, an additional simultaneous catalytic dehydrogenation is required.

In all cases it was surprising that this reaction proceeded in high yields, selectivities and space time yields.

Starting compounds of formula II are 5-formylvaleric acid and 6-hydroxycaproic acid and esters thereof, alone or as a mixture with adipic diesters, in which case the esters may contain aliphatic radicals having 1–6 carbon atoms or cycloaliphatic, aromatic radicals or araliphatic radicals having 5–12, preferably 6–8, carbon atoms. Examples of radicals R are methyl, ethyl, propyl, isopropyl, butyl, isobutyl, tert-butyl, hexyl, cyclopentyl, cyclohexyl, phenyl or benzyl radicals.

Examples of compounds of the formula II which may be used as starting materials include: 5-formylvaleric acid, 6-hydroxycaproic acid, methyl 5-formylvalerate, ethyl 5-formylvalerate, isobutyl 5-formylvalerate, cyclohexyl 5-formylvalerate, benzyl 5-formylvalerate, phenyl 5-formylvalerate, 6-hydroxycaproic acid, methyl 6-hydroxycaproate, propyl 6-hydroxycaproate, n-butyl 6-hydroxycaproate, cyclopentyl 6-hydroxycaproate, phenyl 6-hydroxycaproate, alone or as a mixture with dimethyl adipate, diethyl adipate or di-n-butyl adipate.

It is also possible to use mixtures of compounds of the formula II featuring both formyl and hydroxymethyl groups as starting compounds.

Further possible starting compounds are compounds which are converted into compounds of the formula II under the reaction conditions. For example, mixtures of caprolactone and water or alcohols may be used instead of 6-hydroxycaproic acid or 6-hydroxycaproic esters. If, for example in the reaction of 6-hydroxycaproic esters according to the invention, caprolactone is byproduced, it can be separated off and recycled.

5-Formylvaleric acid to be used as a starting compound may be obtained by hydroformylation of 3- and 4-pentenoic acid, for example as described in WO 97/08127. 5-Formylvaleric esters may be obtained by hydroformylation of 3- and 4-pentenoic esters, for example as described in EP-A 556 681.

6-Hydroxycaproic acid and 6-hydroxycaproic esters are formed, for example, by hydrolysis or alcoholysis of caprolactone.

In a particular embodiment, mixtures of 6-hydroxycaproic esters and adipic diesters are used as obtained, for example, by the processes described in DE-A 19 607 954, in which case further compounds may be present in addition to 6-hydroxycaproic esters and adipic diesters, such as caprolactone, 6-alkoxycaproic esters, glutaric diesters, 5-hydroxyvaleric esters, 2-oxocaproic esters, 1,2-cyclohexanediols, valerolactone, unsaturated adipic diesters, for example dihydromuconic diesters, 3-hydroxypentanoic esters, 4-oxopentanoic esters and 5-oxohexanoic esters. These compounds generally neither adversely affect the reaction according to the invention nor, surprisingly, give rise to a deterioration in product quality after purification by distillation.

The proportion of adipic diester in the mixture to be reacted is typically up to 95, preferably up to 90, % by weight.

Suitable catalysts are acidic or basic catalysts, but also catalysts having both acidic and basic properties. When 6-hydroxycaproic acid or an ester thereof is used as starting compound, the catalysts must also have dehydrogenating properties.

For the purposes of the present invention, oxidic catalysts are not only oxides in the narrow sense but also complex oxygen-containing compounds which have intrinsic acidic or basic properties or may be doped accordingly. Hence it is also possible to use heteropolyacids, for example applied to a carrier, zeolites, which are present in the H-form for acidic activity and which are doped with alkali for basic activity, metal phosphates or compounds such as carbonates or hydroxides which can be converted into oxides.

Examples of oxidic catalysts are oxides of elements of groups 1–14 of the Periodic Table of the Elements or rare earth metal oxides or mixtures thereof. For example, use may be made of alkali metal oxides such as sodium oxide, alkaline earth metal oxides, such as magnesium oxide, calcium oxide, barium oxide, furthermore boron trioxide, aluminum oxide, silicon dioxide, for example in the form of silica gel, fused silica, silicates or quartz, furthermore tin dioxide, bismuth oxide, copper oxide, zinc oxide, lanthanum oxide, titanium dioxide, zirconium dioxide, vanadium oxides, chromium oxides, molybdenum oxides, tungsten oxides, manganese oxides, iron oxides, cerium oxides, neodymium oxides or mixtures thereof. The catalysts may also be modified by applying additives, such as acids (for example phosphoric acids) or bases (for example sodium hydroxide).

Specific examples are $La_2O_3$, $ZrO_2$, $Cr_2O_3/ZrO_2$, $CaO/ZnO$, $MgO/ZnO$, $K_2O/TiO_2$, $La_2O_3/Al_2O_3$ and $ZrO_2—SO_4$.

The heteropolyacids to be used according to the invention contain, as essential element, tungsten or preferably molybdenum, which may be partially replaced by vanadium. If vanadium is used, V:Mo atomic ratios of 1:6–1:12 are preferred. Examples of central atoms are phosphorus, silicon, arsenic, germanium, boron, titanium, cerium, thorium, manganese, nickel, tellurium, iodine, cobalt, chromium, iron, gallium, vanadium, platinum, beryllium and zinc. Phosphorus and silicon are preferred. A preferred ratio of molybdenum or tungsten atoms to the respective central atom is 2.5:1–12:1, preferably 11:1–12:1.

Specific examples of molybdenum-containing heteropolyacids are the following compounds:
dodecamolybdophosphoric acid ($H_3PMO_{12}O_{40}$ *n $H_2O$),
dodecamolybdosilicic acid ($H_4SiMo_{12}O_{40}$ *n $H_2O$),
dodecamolybdoceric(IV) acid ($H_8CeMo_{12}O_{42}$ *n $H_2O$),
dodecamolybdoarsenic(V) acid ($H_3AsMo_{12}O_{42}$ *n $H_2O$),
hexamolybdochromic(III) acid ($H_3CrMo_6O_{24}H_6$ *n $H_2O$),
hexamolybdonickelic(II) acid ($H_4NiMo_6O_{24}H_6$ *5 $H_2O$),
hexamolybdoiodic acid ($H_5JMo_6O_{24}$ *n $H_2O$),
octadecamolybdodiphosphoric acid ($H_6P_2Mo_{18}O_{62}$ *11 $H_2O$),
octadecamolybdodiarsenic(V) acid ($H_6As_2Mo_{18}O_{62}$ *25 $H_2O$),
nonamolybdomanganic(IV) acid ($H_6MnMo_9O_{32}$ *n $H_2O$),
undecamolybdovanadophosphoric acid ($H_4PMo_{11}VO_{40}$ *n $H_2O$),
decamolybdodivanadophosphoric acid ($H_5PMo_{10}V_2O_{40}$ *n $H_2O$),
hexamolybdohexatungstophosphoric acid ($H_3PMo_6W_6O_{40}$ *n $H_2O$).

It is of course also possible to use mixtures of heteropolyacids. Preference is given to using dodecamolybdophosphoric acid and dodecamolybdosilicic acid.

As well as free heteropolyacids, it is also possible, however, to employ their salts, in particular their alkali metal and alkaline earth metal salts, as catalysts. Preference is given to cesium salts. As with the free acids, corresponding mixtures of their salts may be used.

The heteropolyacids and their salts are known compounds and can be prepared by known methods, for example by the methods described in Brauer (Editor): Handbuch der Praparativen Anorganischen Chemie, Volume III, Enke, Stuttgart, 1981 or by the methods described in Top. Curr. Chem. 76 (1978), 1. Particular preference is given to preparation methods in which no organic solvent is used and which are carried out in aqueous solution instead.

The heteropolyacids prepared in this manner are generally in hydrated form and are free from coordinatively bound water present therein prior to use. This dehydration can advantageously be carried out thermally, for example by the process described in Makromol. Chem. 190 (1989) 929. Depending on the heteropolyacid used, another possible method of dehydration is to dissolve the heteropolyacid in an organic solvent, for example in a dialkyl ether or alcohol, displace the water with the organic solvent from its coordinate bond with the heteropolyacid and remove the water azeotropically with the solvent.

Typically, anhydrous heteropolyacids prepared by these methods are subsequently calcined at from 250 to 500° C., preferably from 280 to 400° C. Depending on the temperature and pressure selected, the heteropolyacids are typically calcined for from 1 hour to 24 hours. The catalysts obtained in this manner can be used directly in the process of the invention.

The heteropolyacid catalysts are preferably applied to a support. To this end, the heteropolyacid is applied to a support material such as active carbon, silicon dioxide, titanium dioxide or zirconium dioxide by methods known per se, for example by impregnating the relevant support material with a solution of the heteropolyacid in a solvent, preferably water, and subsequently drying under reduced pressure at from 100 to 250° C., preferably from 130 to 250° C., until water can no longer be detected in the catalyst. Anhydrous heteropolyacids prepared by these methods are subsequently calcined at temperatures of from 250 to 500° C., preferably from 280 to 400° C.

Suitable zeolites include any zeolites having basic or acidic centers.

In the case of zeolites having basic properties, zeolites containing alkali metals or alkaline earth metals are used, for example; in the case of zeolites having acidic properties, zeolites in the acidic H-form are used, in which the alkali metal ions are replaced by hydrogen ions.

Preference is given to 12-ring zeolites of the structure type BETA, Y, EMT and Mordenite, and 10-ring zeolites of the Pentasil type. As well as the elements aluminum and silicon, zeolites can also contain boron, gallium, iron or titanium in their framework. Furthermore, they can also be partially ion-exchanged with elements of the groups 3 and 8 to 13 and the lanthanide elements.

Zeolites to be used as catalyst include zeolites of the structure type MFT, MEL, BOG, BEA, EMT; MOR, FAU, MTW, LTL, NES, CON or MCM-22 according to the structure classification given in W. M. Meier, D. H. Olson, Ch. Baerlocher, Atlas of Zeolite Structure Types, Elsevier, 4$^{th}$ ed., 1996.

Particular examples are the zeolites ZBM-20, Fe—H-ZSM5, Sn-beta zeolite, beta zeolite, Zr-beta zeolite, H-beta zeolite, H-mordenite, USY, Ce—V zeolite, H—Y zeolite, Ti/B-beta zeolite, B-beta zeolite or ZB-10.

To obtain very high selectivity, high conversions and long times on stream, it is advantageous to modify the zeolites. A suitable method of modifying the catalysts comprises, for example, doping the shaped or unshaped zeolites with metal salts by ion exchange or impregnation. The metals used are alkali metals such as Li, Cs, K, alkaline earth metals such as Mg, Ca, Sr. Metals of main groups III, IV and V, such as Al, Ga, Ge, Sn, Pb or Bi, transition metals of subgroups IV–VIII such as Ti, Zr, V, Nb, Cr, Mo, W, Mn, Re, Fe, Ru, Os, Co, Rh, Sr, Ni, Pd, Pt, transition metals of subgroups I and II such as Cu, Ag or Zn, and rare earth metals such as La, Ce, Pr, Nd, Er, Yb and U.

Doping is advantageously carried out by introducing the shaped zeolite into a riser pipe and passing an aqueous or ammoniacal solution of a halide or nitrate of the abovementioned metals over it at from 20 to 100° C. Such an ion exchange can take place with the hydrogen, ammonium or alkali metal form of the zeolite. Another way of applying metal to the zeolite comprises impregnating the zeolitic material, for example with a halide, nitrate or oxide of one of the abovementioned metals in aqueous, alcoholic or ammoniacal solution. Both ion exchange and impregnation are followed at least by a drying operation or alternatively by another calcination.

A possible embodiment comprises for example dissolving $Cu(NO_3)_2 \times 3\ H_2O$ or $Ni(NO_3)_2 \times 6\ H_2O$ or $Ce(NO_3)_3 \times 6\ H$ $La(NO_3)_2 \times 6\ H_2O$ or $Cs_2CO_3$ in water and impregnating the shaped or unshaped zeolite with this solution for a certain period of time, for example 30 minutes. Water is removed from any supernatant solution in a rotary evaporator. The impregnated zeolite is then dried at about 150° C. and calcined at about 550° C. This impregnating step can be carried out several times in succession until the desired metal content is obtained.

It is also possible to prepare an aqueous $Ni(NO_3)_2$ solution or an ammoniacal $Pd(NO_3)_2$ solution and to suspend the pure pulverulent zeolite therein at from 40 to 100° C. by stirring for about 24 hours. After filtration, drying at about 150° C. and calcination at about 500° C., the zeolitic material thus obtained can be further processed with or without a binder into extrudates, pellets or fluidizable material.

An ion exchange of the zeolite present in the H-form or ammonium form or alkali metal form can be carried out by introducing the zeolite in the form of extrudates or pellets into a column and passing, for example, an aqueous $Ni(NO_3)_2$ solution or ammoniacal $Pd(NO_3)_2$ solution over it in a recycle loop at a slightly elevated temperature of from 30 to 80° C. for from 15 to 20 hours. This is followed by washing out with water, drying at about 150° C. and calcination at about 550° C. With some metal-doped zeolites, for example Pd-, Cu- or Ni-doped zeolites, an aftertreatment with hydrogen is advantageous.

A further method of modifying the zeolite comprises treating the shaped or unshaped zeolitic material with an acid such as hydrochloric acid, hydrofluoric acid or phosphoric acid and/or steam, advantageously, for example, by treating the zeolite in pulverulent form with 1N phosphoric acid at 80° C. for 1 hour. The treatment is followed by washing with water, drying at 110° C./16 h and calcining at 500° C./20 h. Alternatively, before or after being shaped with a binder, zeolites are treated for example at from 60 to 80° C. with from 3 to 25% strength by weight, in particular from 12 to 20% strength by weight, aqueous hydrochloric acid for from 1 to 3 hours. Afterwards, the zeolite thus treated is washed with water, dried and calcined at from 400 to 500° C.

Further catalysts for preparing cyclopentanone are phosphates, in particular aluminum phosphates, silicon aluminum phosphates, iron aluminum phosphates, cerium phosphate, zirconium phosphates, boron phosphate, iron phosphate, calcium phosphate or mixtures thereof.

Suitable aluminum phosphate catalysts for the process according to the invention are in particular aluminum phosphates synthesized under hydrothermal conditions. Examples of suitable aluminum phosphate include APO-5, APO-9, APO-11, APO-12, APO-14, APO-21, APO-25, APO-31 and APO-33.

$AlPO_4$-5(APO-5) is synthesized, for example, by homogeneously mixing orthophosphoric acid with pseudoboehmite (Catapal SB®) in water, adding tetrapropylammonium hydroxide to this mixture, and then reacting in an autoclave under autogenous pressure at about 150° C. for from 20 to 60 h. The $AlPO_4$ is filtered off, dried at from 100 to 160° C. and calcined at from 450 to 550° C. $AlPO_4$-9 (APO-9) is likewise synthesized from orthophosphoric acid and pseudoboehmite, but in aqueous DABCO solution (1,4-diazabicyclo-(2,2,2)-octane) at about 200° C. under autogenous pressure in the course of from 200 to 400 h. If ethylenediamine is used in place of DABCO solution, APO-12 is obtained.

$AlPO_4$-21 (APO-21) is synthesized from orthophosphoric acid and pseudo boehmite in aqueous pyrrolidine solution at from 150 to 200° C. under autogenous pressure in the course of from 50 to 200 h.

The process according to the invention can also be carried out with known silicon aluminum phosphates such as SAPO-5, SAPO-11, SAPO-31 and SAPO-34. These compounds are prepared by crystallization from aqueous mixture at from 100 to 250° C. and under autogenous pressure in the course of from 2 hours to 2 weeks, the reaction mixture, comprising a silicon, an aluminum and a phosphorus component, being converted in an aqueous solution comprising amine.

SAPO-5 is obtained, for example, by mixing a suspension of $SiO_2$ in an aqueous tetrapropylammonium hydroxide solution with an aqueous suspension of pseudoboehmite and orthophosphoric acid and then reacting at from 150 to 200° C. under autogenous pressure in a stirred autoclave for from 20 to 200 h. The powder is filtered off, dried at from 110 to 160° C. and calcined at from 450 to 550° C. Suitable silicon aluminum phosphates also include ZYT-5, ZYT-6, ZYT-7, ZYT-9, ZYT-11 and ZYT-12. A precipitated aluminum phosphate can also be used in the process as a phosphate catalyst.

For example, such an aluminum phosphate is prepared by dissolving 92 g of diammonium hydrogen phosphate in 700 ml of water. 260 g of $Al(NO_3)_3 \times 9\ H_2O$ in 700 ml of water are added dropwise to this solution in the course of 2 h, during which pH 8 is maintained by adding 25% strength $NH_3$ solution at the same time. The resulting precipitate is subsequently stirred for 12 hours and then filtered off with suction and washed. It is dried at 60° C./16 h.

A boron phosphate catalyst for use in the process according to the invention can be prepared, for example, by mixing and kneading concentrated boric acid and phosphoric acid and subsequently drying and calcining in an inert gas, air or steam atmosphere at from 250 to 650° C., preferably at from 300 to 500° C.

$CePO_4$ is obtained by precipitating from 52 g of $Ce(NO_3)_3 \times 6\ H_2O$ and 56 g of $NaH_2PO_4 \times 2\ H_2O$. The material is filtered off and shaped into extrudates, which are dried at 120° C. and calcined at 450° C. Suitable phosphates for the process according to the invention also include $SrHPO_4$, $FePO_4$ and $Zr_3(Po_4)_4$.

The catalysts described here can be used, for example, in the form of from 2 to 4 mm extrudates or as tablets having a diameter of, for example, from 3 to 5 mm, or as granules having particle sizes of, for example, from 0.1 to 0.5 mm, or in a fluidizable form.

When hydroxycaproic acid is used, additional metals such as copper or silver on oxidic carriers such as metal oxides are typically used to provide the catalysts with dehydrogenation activity.

It has been found that the use of basic catalysts leads to increased formation of cyclopentanone, whereas the use of catalysts having acidic properties leads to increased formation of cyclopentene-1-carboxylic esters I.

The reaction according to the invention may be carried out without water. The addition of water leads to an increased selectivity and time on stream. The molar ratio of starting compound II to water is advantageously 1:0–1:20, in particular 1:0.1–1:5.

The reaction can be carried out in the gas or liquid phase with or without diluents. Examples of suitable diluents are solvents which are completely or substantially inert under the reaction conditions, for example ether such as dioxane or tetrahydrofuran and alcohols such as methanol and ethanol. A gas stage procedure is preferred, provided that easily volatilizible starting materials are used.

The reaction can be carried out batchwise or continuously as a fixed bed reaction with a fixed bed catalyst, for example in an upflow or downflow process in the liquid or gas phase, or as a fluidized bed reaction with the catalyst in the fluidized state in the gas phase, or with a catalyst suspended in the liquid phase.

The reaction is carried out at from 200 to 450° C., preferably from 250 to 390° C., in particular from 300 to 380° C. The reaction is generally carried out under atmospheric pressure. However, it is also possible to use slightly reduced or slightly elevated pressure, for example up to 20 bar. The space velocity is generally in the range from 0.01 to 40, preferably from 0.1 to 20, g of compound of the formula II per gram of catalyst per hour.

The liquid-phase reaction is carried out, for example, by heating a mixture of the starting compound II with or without water to the desired reaction temperature in the presence of a suspended fixed-bed catalyst. After the required reaction time, the reaction mixture is cooled down and the catalyst removed, for example by filtration. The reaction mixture is then subjected to a fractional distillation to recover the products of value and the unconverted ester. The reaction products formed in the course of the reaction can also be continuously removed from the reaction mixture by distillation.

In a preferred embodiment of the process according to the invention in the gas phase, a mixture of starting compound II with or without water is initially vaporized and then passed, with or without hydrogen or an inert gas, such as nitrogen, carbon dioxide or argon, in gaseous form into a fluidized catalyst bed at the desired reaction temperature.

In another preferred embodiment of the process according to the invention in the gas phase, for example, a mixture of the starting compound II with or without water is initially vaporized and then passed, with or without an inert gas, such as nitrogen, carbon dioxide or argon, in gaseous form over a fixed catalyst bed in an upflow or downflow process at the desired reaction temperature.

The reaction effluent is condensed by means of suitable cooling devices and then worked up by fractional distillation. Unconverted starting compounds may be recycled.

Cyclopentanone obtained by the process of the present invention is a useful intermediate. For instance, reductive amination gives cyclopentylamine which is of interest for the synthesis of crop protection agents and pharmaceuticals.

Cyclopentene-1-carboxylic esters are useful building blocks for the synthesis of intermediates.

EXAMPLE

The percentages indicated to characterize the catalysts are by weight.

a) Catalyst Preparation:

| | |
|---|---|
| $ZrO_2$: | obtained from Norton (SN 9516321); directly used as such. |
| $La_2O_3$ (3% of La)/$ZrO_2$ | $ZrO_2$ (Norton, SN 9516321) was impregnated with $La(NO_3)_3$ solution, dried at 120° C. for 4 hours and calcined at 400° C. for 6 hours. |
| $La_2O_3$ (10% of La)/($\alpha$-$Al_2O_3$) | $\alpha$-$Al_2O_3$ (Norton) was impregnated with La $(NO_3)_3$ solution, dried at 120° C. for 4 hours and calcined at 400° C. for 6 hours. |
| 95% of ZnO/5% of MgO | obtained from BASF (H5-10) |
| 56% of ZnO/44% of CaO | obtained from BASF (H5-11) |
| $Al_2O_3$ | obtained from BASF (D 10-10) | b) Experimental Procedure for the Examples of Table 1:

100ml of a catalyst were covered with 30 ml of quartz rings as vaporizing section in a gas phase reactor. 10 g of starting material, corresponding amounts of water (Table 1), methanol or 50 standard liters of nitrogen, respectively (Examples 18–22), or hydrogen (Examples 1–17) were passed over a catalyst in a downflow procedure at the indicated temperatures. The reaction effluents were condensed in a receiver using dry ice/acetone. The compositions of the reaction effluent and thus the conversions and selectivities were determined by gas chromatography (Table 1).

TABLE 1

| Example | Starting material | Cat. | $H_2O$ [moles][e] | Temp. [° C.] | Conversion [%] | Selectivity [%] | |
|---|---|---|---|---|---|---|---|
| | | | | | | CPO[a] | MECPC[b] |
| 1 | ME – 5 – FV[c] | $La_2O_3$ (3% of La) $ZrO_2$ | 0 | 300 | 52 | 33.1 | 38.5 |
| 2 | | | 0 | 350 | 99 | 38.5 | 14 |
| 3 | | $ZrO_2$ | 0 | 270 | 40 | 11.5 | 68.3 |
| 4 | | | 0 | 300 | 48.5 | 14.2 | 68.3 |
| 5 | | | 0 | 330 | 68.9 | 19.5 | 60.5 |
| 6 | | 95% of ZnO/5% of MgO | 0 | 270 | 28.1 | 51.9 | 2.0 |
| 7 | | | 0 | 300 | 16.6 | 59.3 | 1.8 |
| 8 | | | 0 | 330 | 15.0 | 63.8 | 6.7 |
| 9 | | 56% of ZnO/44% of CaO | 0 | 270 | 16.2 | 59.7 | 4.6 |

TABLE 1-continued

| Example | Starting material | Cat. | H₂O [moles]ᵉ | Temp. [°C.] | Conversion [%] | Selectivity [%] CPOᵃ | Selectivity [%] MECPCᵇ |
|---|---|---|---|---|---|---|---|
| 10 |  |  | 0 | 300 | 30.3 | 38.9 | 2.1 |
| 11 |  |  | 0 | 330 | 47.4 | 43.8 | 2.0 |
| 12 |  | Al₂O₃ | 0 | 270 | 48.6 | 23.0 | 17.6 |
| 13 |  |  | 0 | 300 | 47.3 | 24.7 | 48.9 |
| 14 |  |  | 0 | 330 | 61.7 | 34.2 | 24.0 |
| 15 |  | La₂O₃ (10% of La)/ | 0 | 300 | 35.7 | 61.0 | 3.9 |
| 16 |  | α-Al₂O₃ | 0 | 330 | 42.0 | 69.0 | 4.7 |
| 17 |  |  | 0 | 360 | 62.0 | 65.7 | 3.1 |
| 18 | ME – 6 - HCᵈ | 56% of ZnO/44% of CaO | 6 | 350 | 90.1 | 40.7 | 4.3 |
| 19 |  |  | 6 | 380 | 91.1 | 72.6 | 2.4 |
| 20 |  |  | 0 | 380 | 97.1 | 41.8 | 3.9 |
| 21 | Caprolactone | 56% of ZnO/44% of CaO | 3 MeOH | 380 | 65.6 | 47.9 | 15.5 |
| 22 | Caprolactone | 95% ZnO/5% MgO | 3 MeOH | 380 | 69.8 | 32.7 | 25.8 |

ᵃCPO = Cyclopentanone;
ᵇMECPC = Cyclopentene-1-carboxylic acid and its methyl ester;
ᶜME – 5-FV = Methyl 5-formylvalerate;
ᵈME – 6-HC = Methyl 6-hydroxycaproate;
ᵉbased on moles of ester or caprolactone used Experimental Procedure for the Examples in Table 2:

The starting materials indicated in Table 2 are obtained from stage 12 of the process described in DE-A 19 607 954. 100 ml of a catalyst composed of 56% by weight of ZnO and 44% by weight of CaO (BASF: H 5–11) were covered with 30 ml of quartz rings as vaporizing section in a gas phase reactor. 10 g of the starting materials indicated in Table 2 and 20 standard liters of nitrogen were passed over the catalyst in a downflow procedure at 380–400° C. The reaction effluents were condensed in a receiver using dry ice/acetone. The reaction effluent was collected over a period of 7 hours. The stated cyclopentanone selectivity is based on dimethyl adipate, methyl 6-hydroxycaproate and, if used, caprolactone converted.

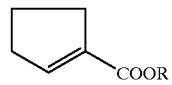

I where R is hydrogen or an aliphatic radical having 1–6 carbon atoms or a cycloaliphatic, araliphatic or aromatic radical having 6–12 carbon atoms, which comprises heating a compound of the formula II

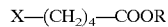

X—(CH₂)₄—COOR    II where X is formyl or hydroxymethyl and R is defined as above, and/or a compound which is converted into a com-

TABLE 2

| Example | Starting material | Catalyst | H₂O added (moles per mole of starting material) | Temperature [°C.] | Conversion [%] | Cyclopentanone selectivity [%] |
|---|---|---|---|---|---|---|
| 23 | ME – 6-HC | 56% of ZnO, 44% of CaO | 3 | 380 | 98.1 | 67.7 |
| 24 | 1:1¹⁾ |  |  |  | 93.5 | 90.0 |
| 25 | 2:1¹⁾ |  |  |  | 92.5 | 67.3 |
| 26 | 4:1¹⁾ |  |  |  | 94.8 | 61.5 |
| 27 | Ester mixture²⁾ |  |  |  | 79.4 | 68.4 |
| 28 |  |  | 0 |  | 29.2 | 76.4 |
| 29 |  |  | 6 | 400 | 66.9 | 82.2 |

DMA = Dimethyl adipate; ME – 6-HC = Methyl 6-hydroxycaproate
¹⁾Molar ratio DMA:ME – 6-HC
²⁾Ester mixture:

| | % by weight |
|---|---|
| Dimethyl adipate | 59.2 |
| Methyl 6-hydroxycaproate | 14.6 |
| Caprolactone | 1.4 |
| Methyl 6-methoxycaproate | 0.3 |
| Dimethyl glutarate | 6.7 |
| Methyl 2-oxocaproate | 2.2 |
| Methyl 5-hydroxyvalerate | 2.0 |
| Dimethyl dihydromuconate | 2.4 |
| 1,2-cyclohexanediol | 0.5 |
| δ-valerolactone | 2.4 |

We claim:

1. A process for preparing cyclopentanone and cyclopentene-1-carboxylic acid or an ester thereof of the formula I pound of the formula II by reaction with water or alcohols ROH under the reaction conditions to from 200 to 450° C. in the gas or liquid phase in the presence of a heterogeneous oxidic catalyst.

2. A process as claimed in claim 1, wherein a compound of the formula II is reacted in a mixture with an adipic diester of the formula III $$ROCO-(CH_2)_4-COOR \qquad III,$$

where R is defined as above.

3. A process as claimed in claim 1, wherein the compound which is converted into a compound of the formula II is ε-caprolactone.

4. A process as claimed in claim 1, wherein the starting material used is a mixture of 6-hydroxycaproic ester and adipic diester.

5. A process as claimed in claim 1, wherein water is added to the reaction mixture.

6. A process as claimed in claim 1, wherein the catalyst used when using hydroxycaproic acid or a hydroxycaproic ester has additional dehydrogenation activity.

7. A process as claimed in claim 1, wherein a basic oxidic catalyst is used to give predominantly cyclopentanone.

8. A process as claimed in claim 1, wherein an acidic oxidic catalyst is used to give predominantly cyclopentene carboxylic acid or an ester thereof.

9. A process as claimed in claim 1, wherein the catalyst used is a zeolite.

10. A process as claimed in claim 1, wherein the catalyst used is a heteropolyacid.

11. A process as claimed in claim 1, wherein the catalyst used is a phosphate.

12. A process as claimed in claim 1, wherein the catalyst used is a metal oxide of groups 1–14 of the Periodic Table of the Elements and/or a lanthanide oxide.

* * * * *